United States Patent
Teles et al.

(10) Patent No.: US 9,926,248 B2
(45) Date of Patent: Mar. 27, 2018

(54) PROCESS FOR THE PREPARATION OF 3-HEPTANOL FROM A MIXTURE CONTAINING 2-EHTHYLHEXANAL AND 3-HEPTYL FORMATE

(71) Applicant: BASF SE, Ludwigshafen (DE)

(72) Inventors: Joaquim Henrique Teles, Waldsee (DE); Joachim Simon, Ludwigshafen (DE); Martine Dehn, Ludwigshafen (DE); Manuel Danz, Plankstadt (DE); Richard Dehn, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/902,247

(22) PCT Filed: Jun. 25, 2014

(86) PCT No.: PCT/EP2014/063397
§ 371 (c)(1),
(2) Date: Dec. 30, 2015

(87) PCT Pub. No.: WO2015/000762
PCT Pub. Date: Jan. 8, 2015

(65) Prior Publication Data
US 2016/0368843 A1  Dec. 22, 2016

Related U.S. Application Data

(60) Provisional application No. 61/841,942, filed on Jul. 2, 2013.

(30) Foreign Application Priority Data

Jul. 2, 2013 (EP) .................................. 13174705

(51) Int. Cl.
C07C 29/16 (2006.01)
C07C 29/88 (2006.01)
C07C 29/09 (2006.01)

(52) U.S. Cl.
CPC ............ C07C 29/16 (2013.01); C07C 29/095 (2013.01); C07C 29/88 (2013.01)

(58) Field of Classification Search
CPC ........ C07C 29/095; C07C 29/16; C07C 29/88
See application file for complete search history.

(56) References Cited

U.S. PATENT DOCUMENTS

| | | |
|---|---|---|
| 3,796,732 A | 3/1974 | Brenner |
| 6,262,311 B1 | 7/2001 | Maassen et al. |
| 2012/0090226 A1* | 4/2012 | Lamoureaux ............. C10L 1/02 44/452 |

FOREIGN PATENT DOCUMENTS

| | | |
|---|---|---|
| DE | 2 221 624 A1 | 11/1972 |
| DE | 2 139 692 A1 | 2/1973 |
| EP | 127 888 A1 | 12/1984 |
| EP | 167 153 A1 | 1/1986 |
| EP | 0 216 351 A2 | 4/1987 |
| EP | 294 584 A1 | 12/1988 |
| EP | 0369823 A1 | 5/1990 |
| EP | 0475272 A2 | 3/1992 |
| EP | 1 092 701 A1 | 4/2001 |
| JP | 55072136 | 5/1980 |

OTHER PUBLICATIONS

Glinski et al., "Oxidation of 2-ethylhexanal in the liquid phase," React. Kinet. Catal. Lett. vol. 55, No. 2, 311-318 (1995).*
Robinson et al., "Reactions of diethoxytriphenylphosphorane with diastereoisomeric 3-methylcyclohexane-1,2-diols. Control of regioselectivity by methyl substitution during cyclodehydration and rearrangement of 1,2-diols," J. Org. Chem. 1985, 50, 3860-3863.*
Cadierno et al, "Ruthenium-catalyzed redox isomerization/transfer hydrogenation in organic and aqueous media: A one-pot tandem process for the reduction of allylic alcohols," Green Chem., 2009, 11, 1992-2000.*
Hausermann, M., "148. Zur Disproportionierung aliphatischer Aldehyde", Helvetica Chimica Acta, vol. 34, pp. 1211-1215.
International Search Report for PCT/EP2014/063397 dated Oct. 10, 2014.

* cited by examiner

*Primary Examiner* — Pancham Bakshi
*Assistant Examiner* — Mark P Luderer
(74) *Attorney, Agent, or Firm* — Drinker Biddle & Reath LLP

(57) ABSTRACT

The invention relates to a method for producing 2,3,5-trimethyl benzoquinone or a compound containing 2,3,5-trimethyl benzoquinone, the method comprising the following steps: Oxidation of 2,3,6-trimethylphenol with oxygen or an oxygen-containing gas in a two- or multi-phase reaction medium in the presence of a catalyst or catalyst system containing at least one copper (II)-halide to a mixture containing 2,3,5-trimethyl benzoquinone, characterized in that the reaction medium contains water and at least one secondary aliphatic acyclic alcohol having 6 or more, preferably 7 or more, carbon atoms.

21 Claims, No Drawings

PROCESS FOR THE PREPARATION OF 3-HEPTANOL FROM A MIXTURE CONTAINING 2-EHTHYLHEXANAL AND 3-HEPTYL FORMATE

CROSS-REFERENCE TO RELATED APPLICATIONS

This application is a national stage application (under 35 U.S.C. § 371) of PCT/EP2014/063397, filed Jun. 25, 2014, which claims benefit of European Application No. 13174705.7, filed Jul. 2, 2013, and U.S. Application No. 61/841,942, filed Jul. 2, 2013, all of which are incorporated herein by reference in their entirety.

The present invention relates to a process for the preparation of 3-heptanol or of a mixture comprising 3-heptanol, comprising the following step: (i) addition of an aqueous solution (A) comprising one or more alkali metal hydroxide(s) to a mixture (B) at least comprising 2-ethylhexanal and 3-heptyl formate, wherein the concentration of the alkali metal hydroxide/alkali metal hydroxides in the aqueous solution (A) is at least 40% by weight.

A further aspect of the present invention relates to a mixture comprising 3-heptanol, where the mixture is preferably preparable or prepared by the process according to the invention, and where the mixture comprises 2-ethylhexanal and 3-heptyl formate in a total concentration of <5% by weight, preferably <2% by weight, based on the mixture.

3-Heptanol can be obtained industrially e.g. as a byproduct from the low-boiler stream during the preparation of 2-ethylhexanoic acid. Said low-boiler stream is produced during the distillation of the reaction discharge after oxidation of 2-ethylhexanal to 2-ethylhexanoic acid has taken place and as a rule comprises about 50-60% by weight of 3-heptyl formate, 5-10% by weight of 3-heptanol, 10-15% by weight of heptanones (3-/4-heptanone), 10-20% by weight of 2-ethylhexanal, and 2-5% by weight of 2-ethylhexanoic acid.

3-Heptanol can be enriched in the low-boiler stream through basic hydrolysis of 3-heptyl formate. However, distillative removal of the resulting 3-heptanol from the low-boiler stream is not possible with reasonable expenditure particularly on account of the 2-ethylhexanal that is still present in the low-boiler stream.

DE 2 139 692 describes a process for obtaining 3-heptanol from the above-described low-boiler stream of the 2-ethylhexanoic acid preparation. It is a two-stage process which can be carried out discontinuously or continuously. In the first step, the complete or partial removal of the add present in the mixture takes place by means of water or dilute alkali metal hydroxide solution. Hydrogenation in the presence of a hydrogenation catalyst then takes place.

Following final distillation, yields of approx. 80% of 3-heptanol, based on the 3-heptyl formate, 3-heptanol and 3-heptanone present in the feed material are obtained by this two-stage process. The continuous hydrogenation is described with a yield of 78%.

A disadvantage of the process described in DE 2 139 692 is the required high hydrogen pressures of up to 400 bar, as a result of which the hydrogenation can only be carried out in special ultrahigh-pressure reactors. These are associated with relatively high capital costs for setting up the plant and increased production outputs as a result of the two-stage process procedure.

The object of the present invention is therefore to provide a process for the preparation of 3-heptanol from the low-boiler stream of the 2-ethylhexanoic acid production which avoids the disadvantages described above. In particular, it is an object of the present invention to provide a process for the preparation of 3-heptanol from the low-boiler stream of the 2-ethylhexanoic acid production in which the yield of 3-heptanol, based on the feed material, can be increased.

Surprisingly, it has been found that the removal of the 2-ethylhexanal from the reaction mixture by means of direct reaction with alkali metal hydroxide solution at atmospheric pressure or at a slight superatmospheric pressure, with the simultaneous hydrolysis of the 3-heptyl formate to 3-heptanol, is possible if the concentration of the added hydroxide solution is ≥40% by weight.

The present invention therefore provides a process for the preparation of 3-heptanol or of a mixture comprising 3-heptanol comprising the following step (i): addition of an aqueous solution (A) comprising one or more alkali metal hydroxide(s) to a mixture (B) at least comprising 2-ethylhexanal and 3-heptyl formate, wherein the concentration of the alkali metal hydroxide/alkali metal hydroxides in the aqueous solution (A) is at least 40% by weight.

In the examples listed in DE 2 139 692, the low-boiler stream is treated with water and dilute sodium hydroxide solution at 30° C. in order to remove the carboxylic acids present. The high ester value and the low OH value of the oil phase obtained after subsequent phase separation clearly show that no or only slight hydrolysis of the formate has taken place under these conditions. The reaction of the formate accordingly takes place during the hydrogenation, with the ketones and aldehydes present in the mixture being converted at the same time to the corresponding secondary or primary alcohols.

Surprisingly, it has been found that under the reaction conditions of the process according to the invention, possibly on account of the strong steric demand of the ethyl group in the alpha position to the carbonyl group, no homoaldol condensation of the 2-ethylhexanal takes place. Instead, some of the ethylhexanal enters into an aldol condensation with the 3-/4-heptanone likewise present in the mixture. Moreover, 2-ethylhexanol is detected in the reaction discharge, which points to disproportionation of the 2-ethylhexanal. Both the aldol condensation product and the 2-ethylhexanol differ significantly from 3-heptanol in their boiling behavior. I.e., the secondary components a remaining in the reaction discharge, as well as the compounds resulting from the 2-ethylhexanal can then be separated without problem by distillation.

The mixture (B) comprising 2-ethyhexanal and 3-heptyl formate to be used according to the invention can furthermore also comprise 2-ethylhexanoic acid and/or 3-heptanol and/or 3-/4-heptanone.

In a preferred embodiment of the process according to the invention, the mixture (B) consists of the following constituents:
2-ethylhexanal: 10-20% by weight
3-heptyl formate: 50-60% by weight
3-heptanol: 5-1% by weight
3-/4-heptanone: 8-15% by weight
2-ethylhexanoic acid: 2-5% by weight
water: <1% by weight According to the invention, lithium hydroxide, sodium hydroxide, potassium hydroxide, cesium hydroxide or a combination of two or more of these hydroxides can be used as alkali metal hydroxide. In an advantageous embodiment of the process according to the invention, the alkali metal hydroxide/alkali metal hydroxides is/are selected from the group consisting of potassium hydroxide and sodium hydroxide, and combinations thereof.

The concentration of the alkali metal hydroxide/alkali metal hydroxides in the aqueous solution (A) is at least 40% by weight. In an advantageous embodiment of the process according to the invention, the concentration of the alkali metal hydroxide/alkali metal hydroxides in the aqueous solution (A) is at least 45% by weight.

In a further advantageous embodiment of the process according to the invention, the molar amount of the alkali metal hydroxide/alkali metal hydroxides is at least 1.5 times, preferably at least 2 times, the sum of the molar amounts of 3-heptyl formate and 2-ethyhexanal in the mixture (B).

It is preferred according to the invention that the addition of the aqueous solution (A) to the mixture (B) takes place over a period of at least 3 hours.

Moreover, it is preferred according to the invention that after the addition of the aqueous solution (A) to the mixture (B) has taken place, the resulting reaction mixture (C) is stirred over a period of at least 6 hours, preferably over a period of at least 9 hours, particularly preferably over a period of at least 12 hours.

Furthermore, it is preferred according to the invention that the addition of the aqueous solution (A) to the mixture (B) takes place at a temperature of at least 50'C, preferably at a temperature of at least 100*C, particularly preferably at a temperature of at least 120'C.

Moreover, it is preferred according to the invention that the addition of the aqueous solution (A) to the mixture (B) takes place at a pressure of at most 3 bar, preferably at a pressure of at most 1 bar.

After the addition of the aqueous solution (A) to the mixture (B) has taken place, the resulting reaction mixture can be admixed with water in a further reaction step (ii) and the phases that are formed can be separated.

The resulting organic phase can be washed with water in a further reaction step (ill) and optionally then dried, for example with the help of anhydrous sodium sulfate or other suitable drying agents, or by means of stripping/distillation.

As a result of the process according to the invention, the secondary components remaining in the reaction discharge of the oxidation of 2-ethylhexanal to 2-ethylhexanoic acid, as well as the compounds that are formed from the 2-ethylhexanal can be separated without problem by distillation. In an advantageous embodiment of the process according to the invention, the washed and dried organic phase is distilled in a further reaction step (iv) for separation into its constituents.

The present invention further provides a mixture comprising 3-heptanol, where the mixture is preferably preparable or prepared by the process according to the invention, and where the mixture comprises 2-ethylhexanal and 3-heptyl formate in a total concentration of <5% by weight, preferably <2% by weight, based on the mixture.

The present invention will be illustrated in more detail by reference to the following examples.

EXAMPLES 1-12

The feed material used is the untreated low-boiler stream from the preparation of ethylhexanoic acid. The composition of this stream can vary here within the following limits:
3-heptyl formate: 50-60% by weight,
3-heptanol: 5-10% by weight,
2-ethylhexanal: 10-20% by weight,
3-/4-heptanone: 8-15% by weight,
2-ethyhexanoic acid: 2-5% by weight,
water: 0.6-0.9% by weight
The acid value is 43, the ester value is 249.

The base amount (equivalents) stated in each case in table 1 is based on the sum of the molar amounts of 3-heptyl formate, 2-ethylhexanal and 2-ethylhexanoic acid in the feed material, the base concentration is based on the aqueous solution used.

Conversion and yield are determined by means of quantitative GC analysis of the raw material.

The yield of 3-heptanol refers to the sum of 3-heptyl formate and 3-heptanol in the feed material.

General Procedure for Experiments at Atmospheric Pressure (Examples 1 to 10):

The low-boiler forerunning is placed in a 1 L jacketed vessel and heated to the respective temperature. Then, the base is added dropwise as an aqueous solution over 3 h. When the dropwise addition is complete, after-stirring is carried out for the time stated in the table at the stated temperature ('reaction time').

Then, the mixture is admixed with water to dissolve the precipitated salts and the phases are separated at 50° C. Conversion and yield are determined by means of quantitative GC analysis of the organic phase.

General Procedure for Pressure Experiments (Examples 11 and 12):

Low-boiler forerunning and aqueous alkaline metal hydroxide solution are placed in a 300 ml steel autoclave and heated to the respective temperature. Then, after-stirring is carried out for the time stated in the table at the stated temperature ("reaction time").

Then, the mixture is admixed with water to dissolve the precipitated salts, and the phases are separated at 50° C. Conversion and yield are determined by means of quantitative GC analysis of the organic phase.

TABLE 1

Overview of experiments

| Example | Base | Concentration [%] | Equiv. | Temperature [° C] | Pressure [bar] | Reaction time [h] | Conversion of 2-ethylhexanal | Yield of 3-heptanol |
|---|---|---|---|---|---|---|---|---|
| 1 | NaOH | 50 | 3 | 50 | 1 | 21 | 93 | 93 |
| 2 | NaOH | 50 | 3 | 80 | 1 | 12 | 97 | 89 |
| 3 | NaOH | 50 | 3 | 100 | 1 | 12 | 99 | 86 |
| 4 | NaOH | 50 | 3 | 120 | 1 | 6 | 99 | 82 |
| 5 | KOH | 50 | 3 | 120 | 1 | 12 | 99 | 83 |
| 6 | NaOH | 50 | 2 | 100 | 1 | 12 | 94 | 88 |
| 7 | NaOH | 50 | 2 | 120 | 1 | 6 | 94 | 83 |
|  |  |  |  |  |  | 12 | 99 | 81 |
| 8 | NaOH | 50 | 1.5 | 120 | 1 | 12 | 99 | 81 |
| 9 comp. | NaOH | 25 | 2 | 115 | 1 | 21 | 48 | n.d. |
| 10 | NaOH | 40 | 3 | 120 | 1 | 9 | 95 | 87 |
| 11 comp. | NaOH | 30 | 2.5 | 140 | 3 | 12 | 88 | 71 |
| 12 | NaOH | 40 | 2.5 | 140 | 3 | 12 | 99 | 66 |

EXAMPLE 13

2400 g of forerunning from the ethylhexanoic acid preparation (composition: 6.2% by weight of 3-heptanol, 8.4% by weight of 3-heptanone, 1.4% by weight of 4-heptanone, 17.2% by weight of 2-ethylhexanal, 53.9% by weight of 3-heptyl formate, 0.8% by weight of 2-ethylhexanoic acid, 0.9% by weight of water) are placed in an 8 L jacketed vessel made of glass and provided with a mechanical stirrer and heated to 120° C. (reflux) at ambient pressure (stirrer speed 300 rpm). Then, 2960 g of 50% strength aqueous NaOH solution (37 mol, 3 mol/mol) are added dropwise over 60 min and the mixture is then heated for a further 6 h under reflux. The resulting suspension is admixed with 1500 g of water and cooled to 80° C. The phases are then separated. The organic phase is washed a further time with 1500 g of water and dried over anhydrous, pulverulent sodium sulfate (approx. 15 g).

After removing the sodium sulfate by filtration, 1853 g of a clear, slightly yellow liquid are obtained (acid value 0.5, ester value 4). The content of 3-heptanol is determined by means of calibrated GC analysis as 50.1%, corresponding to a yield of 78% based on the sum of 3-heptanol and 3-heptyl formate in the feed material.

150 g of the material thus obtained are distilled over a column with reflux divider (height 210 mm, diameter 22 mm), which is filled with 3 mm glass rings, at a head pressure of 20 mbar. 53.4 g of 3-heptanol are obtained at a head temperature of 61-63° C. (purity>98%).

The invention claimed is:

1. A process for the preparation of 3-heptanol or of a mixture comprising 3-heptanol, comprising the following step:
   (i) adding an aqueous solution (A) comprising one or more alkali metal hydroxide(s) to a mixture (B) at least comprising 2-ethylhexanal and 3-heptyl formate,
   wherein the concentration of the alkali metal hydroxide/alkali metal hydroxides in the aqueous solution (A) is at least 40% by weight.

2. The process according to claim 1, wherein the mixture (B) furthermore comprises one, two or all of the compounds selected from the group consisting of 2-ethylhexanoic acid, 3-heptanol and 3-heptanone.

3. A process for the preparation of 3-heptanol or of a mixture comprising 3-heptanol, comprising the following step:
   (i) adding an aqueous solution (A) comprising one or more alkali metal hydroxide(s) to a mixture (B) at least comprising 2-ethylhexanal and 3-heptyl formate,
   wherein the concentration of the alkali metal hydroxide/alkali metal hydroxides in the aqueous solution (A) is at least 40% by weight and
   wherein the mixture (B) consists of the following constituents:
   2-ethylhexanal: 10-20% by weight
   3-heptyl formate: 50-60% by weight
   3-heptanol: 5-10% by weight
   3/4-heptanone: 8-15% by weight
   2-ethylhexanoic acid: 2-5% by weight
   water: <1% by weight.

4. The process according to claim 1, wherein the alkali metal hydroxide/alkali metal hydroxides is/are selected from the group consisting of potassium hydroxide and sodium hydroxide, and combinations thereof.

5. The process according to claim 1, wherein the concentration of the alkali metal hydroxide/alkali metal hydroxides in the aqueous solution (A) is at least 45% by weight.

6. The process according to claim 1, wherein the molar amount of the alkali metal hydroxide/alkali metal hydroxides is at least 1.5 times the sum of the molar amounts of 3-heptyl formate, 2-ethylhexanal and 2-ethylhexanoic acid in the mixture (B).

7. The process according to claim 1, wherein the molar amount of the alkali metal hydroxide/alkali metal hydroxides is at least 2 times the sum of the molar amounts of 3-heptyl formate, 2-ethylhexanal and 2-ethylhexanoic acid in the mixture (B).

8. The process according to claim 1, wherein the addition of the aqueous solution (A) to the mixture (B) takes place over a period of at least 3 hours.

9. The process according to claim 1, wherein, after the addition of the aqueous solution (A) to the mixture (B) has taken place, the resulting mixture (C) is stirred for a period of at least 6 hours.

10. The process according to claim 1, wherein the addition of the aqueous solution (A) to the mixture (B) takes place at a temperature of at least 50° C.

11. The process according to claim 1, wherein the addition of the aqueous solution (A) to the mixture (B) takes place at a pressure of at most 3 bar.

12. The process according to claim 1, wherein, after the addition of the aqueous solution (A) to the mixture (B) has taken place, the resulting mixture (C) is stirred for a period of at least 12 hours.

13. The process according to claim 1, wherein the addition of the aqueous solution (A) to the mixture (B) takes place at a temperature of at least 120° C.

14. The process according to claim 1, wherein the addition of the aqueous solution (A) to the mixture (B) takes place at a pressure of at most 1 bar.

15. The process according to claim 12, wherein the addition of the aqueous solution (A) to the mixture (B) takes place at a temperature of at least 120° C. and a pressure of at most 1 bar.

16. The process according to claim 1, wherein, after the addition of the aqueous solution (A) to the mixture (B) has taken place, the resulting mixture (C) is admixed in a further reaction step (ii) with water and the phases that are formed are separated.

17. The process according to claim 11, wherein, in a further reaction step (iii), the resulting organic phase is washed with water and is optionally then dried.

18. The process according to claim 12, wherein, in a further reaction step (iv), the washed and optionally dried organic phase is distilled for separation into its constituents.

19. A process for the preparation of 3-heptanol or of a mixture comprising 3-heptanol, consisting essentially of the following step:
   (i) adding an aqueous solution (A) comprising one or more alkali metal hydroxide(s) to a mixture (B) at least comprising 2-ethylhexanal and 3-heptyl formate,
   wherein the concentration of the alkali metal hydroxide/alkali metal hydroxides in the aqueous solution (A) is at least 40% by weight.

20. The process according to claim 2, wherein the mixture comprises 2-ethylhexanal and 3-heptyl formate in a total concentration of <5% by weight based on the mixture.

21. The process according to claim 2, wherein the mixture comprises 2-ethylhexanal and 3-heptyl formate in a total concentration of <2% by weight, based on the mixture.

* * * * *

UNITED STATES PATENT AND TRADEMARK OFFICE
CERTIFICATE OF CORRECTION

PATENT NO. : 9,926,248 B2  
APPLICATION NO. : 14/902247  
DATED : March 27, 2018  
INVENTOR(S) : Joaquim Henrique Teles et al.

Page 1 of 1

It is certified that error appears in the above-identified patent and that said Letters Patent is hereby corrected as shown below:

On the Title Page

Item (54) and in the Specification, Column 1, Lines 1-4, in the title:
PROCESS FOR THE PREPARATION OF 3-HEPTANOL FROM A MIXTURE CONTAINING 2-EHTHYLHEXANAL AND 3-HEPTYL FORMATE Should be:
PROCESS FOR THE PREPARATION OF 3-HEPTANOL FROM A MIXTURE CONTAINING 2-ETHYLHEXANAL AND 3-HEPTYL FORMATE Signed and Sealed this  
Thirteenth Day of November, 2018

Andrei Iancu  
*Director of the United States Patent and Trademark Office*